United States Patent [19]

Kaneko et al.

[11] Patent Number: 5,692,516
[45] Date of Patent: Dec. 2, 1997

[54] SINGLE-NERVE-ACTION-POTENTIAL-MEASURING APPARATUS

[75] Inventors: Hidekazu Kaneko; Shinya Suzuki, both of Tsukuba, Japan

[73] Assignee: Director-General Of Agency Of Industrial Science & Technology, Tokyo, Japan

[21] Appl. No.: 677,847

[22] Filed: Jul. 10, 1996

[30] Foreign Application Priority Data

Jul. 10, 1995 [JP] Japan ................... 7-173080

[51] Int. Cl.$^6$ ........................................ A61B 5/04
[52] U.S. Cl. ............................. 128/731; 128/733
[58] Field of Search ........................... 128/731, 733

[56] References Cited

U.S. PATENT DOCUMENTS

| | | | |
|---|---|---|---|
| 5,178,161 | 1/1993 | Kovacs | 607/2 |
| 5,314,495 | 5/1994 | Kovacs | 607/48 |
| 5,398,187 | 3/1995 | Yamada et al. | 128/731 |
| 5,563,067 | 10/1996 | Sugihara et al. | 435/287.1 |

FOREIGN PATENT DOCUMENTS

| | | | |
|---|---|---|---|
| 650610 | 3/1979 | U.S.S.R. | 128/731 |

OTHER PUBLICATIONS

Z. Nadasdy et al., Society for Neuroscience Abstracts, Recognition of Spatially Separated . . . , vol. 21, part 2, p. 1206, 1995.

Bruce L. McNaughton et al., Journal of Neuroscience Methods, The stereotrode: A new . . . , vol. 8, pp. 391-397, 1983.

*Primary Examiner*—William E. Kamm
*Assistant Examiner*—Carl H. Layno

[57] ABSTRACT

A single-nerve-action-potential-measuring apparatus comprises a multi-channel electrode, a space-damping-vector-calculating section, and a single nerve action potential separating and extraction section. The multi-channel electrode, which consists of multiple bunched micro electrode wires, measures the compound nerve action potential. The space-damping-vector-calculating section evaluates the damping effect corresponding to the distance between the micro electrode wires and nerve cells with no effect from a decrease in the signal-to-noise ratio. The single nerve action potential separating and extracting section extracts only the nerve action potential generated from a particular neuron by clustering the space-damping-vectors. These features enable the apparatus to separate and extract a single-nerve action spike with high precision even under conditions when the signal-to-noise ratio is low or at a site where cells are densely packed.

5 Claims, 3 Drawing Sheets

SINGLE-NERVE-ACTION-POTENTIAL-MEASURING APPARATUS

FIELD OF THE INVENTION

The present invention relates to a single-nerve-action-potential-measuring apparatus for extracting a single-neuron action potential in neuroelectricity physiology experiments.

Background of the Invention

The technique of elucidating brain function from the nerve action potential firing pattern is utilized as a basic means in electrophysiology. In order to elucidate the brain function as executed by a nerve group, it is necessary and essential to elucidate the function of individual neurons (nerve cells), and conventionally there is the single-nerve-activity-measuring method that uses a microelectrode having a high impedance. In the single-nerve-activity-measuring method, an electrode is brought as close as possible to the target cells to be measured, to extract only the activity of a particular neuron based on the difference in the duration or the amplitude of the nerve action spike. However, under conditions when the signal-to-noise ratio is low or at a brain site where cells are densely packed (e.g., at the hippocampus), it is difficult to precisely separate a single nerve action spike.

SUMMARY OF THE INVENTION

An object of the present invention is to provide a single-nerve-action-potential-measuring apparatus capable of separating and extracting the single-nerve action potential precisely even under conditions when the signal-to-noise ratio is low or at a brain site where cells are densely packed.

Other and further objects, features, and advantages of the invention will appear more evident from the following description, taken in connection with the accompanying drawings.

DETAILED DESCRIPTION OF THE INVENTION

The single-nerve-action-potential-measuring apparatus of the present invention comprises a multi-channel microelectrode, for measuring the compound nerve activity, composed of multiple bunched microelectrodes to be inserted into a brain or nerve fascicle; a space-damping-vector-calculating means, for evaluating the damping effect corresponding to the distance between said multiple microelectrodes and nerve cells, based on the multi-channel simultaneously measured data led from said multi-channel microelectrode, with no effect from a decrease in the signal-to-noise ratio; and a single nerve action potential separating and extracting means, for separating and extracting the nerve action potential generated from a particular neuron from other neurons, based on the space-damping vector calculated in the space-damping-vector-calculating means.

Description of the Preferred Embodiment

One of the preferred embodiments of the present invention is described in more detail, with reference to the drawings.

Figure 1:
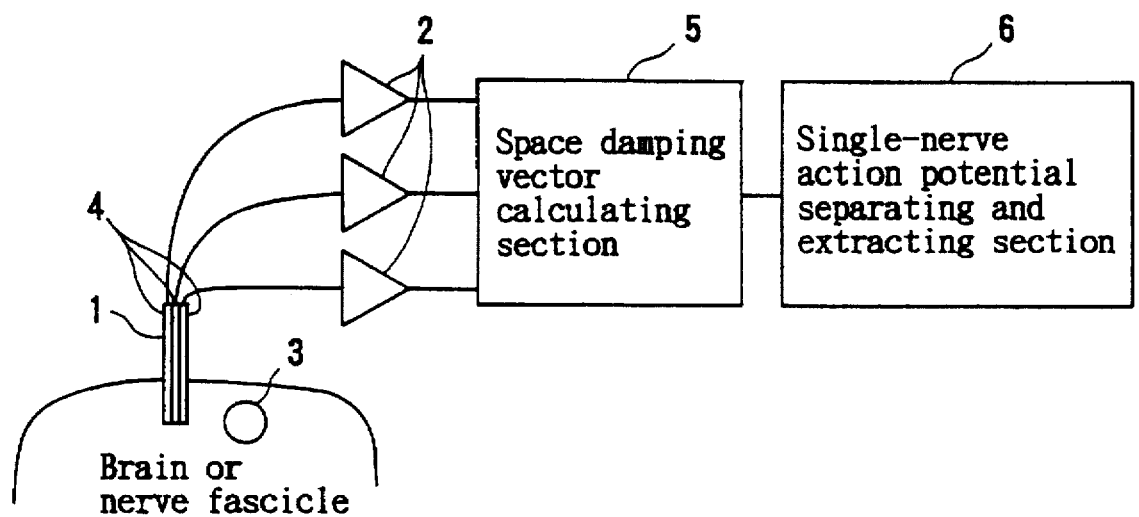
FIG. 1 is a diagram showing an example of the constitution of the single-nerve-action-potential-measuring apparatus of the present invention.

FIG. 1 is a diagram showing an example of the constitution of the single-nerve-action-potential-measuring apparatus of the present invention. Referring to FIG. 1, the single-nerve-action-potential-measuring apparatus comprises a multi-channel microelectrode 1, for measuring the compound nerve action potential, made up of multiple bunched microelectrode wires 4; amplifiers 2, for amplifying respective nerve action potentials led from the wires 4 of the multi-channel microelectrode 1; a space-damping vector-calculating section 5, and a single-nerve action potential separating and extracting section 6.

Herein, the above multi-channel microelectrode 1, for measuring the compound nerve action potential, is made up of multiple microelectrode wires 4 that are bunched and, for example, made by cutting and bunching polyurethane-covered stainless wires 4, having a diameter of 50 microns, the cut surfaces of which can be used for leading the nerve action potentials. Further, as described later, the individual electrode wires 4 serve as channels.

Figure 3:
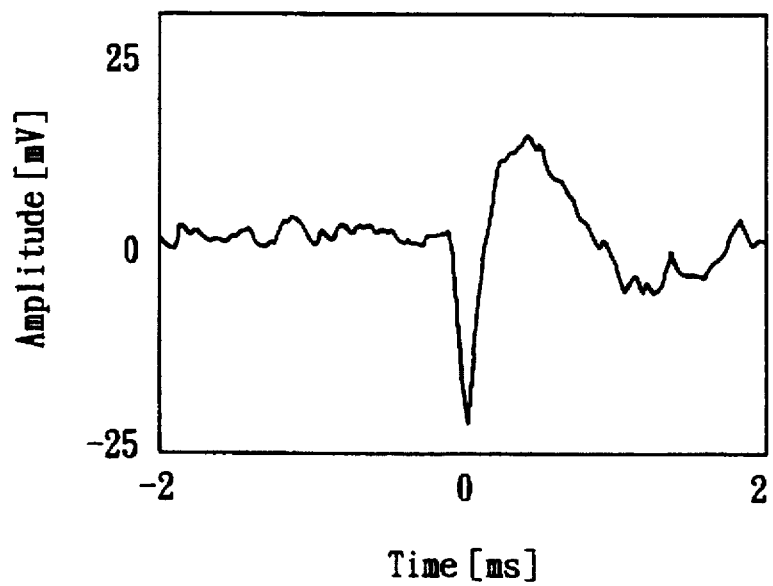
FIG. 3 is a chart showing a template waveform of a nerve action spike.

The above space-damping-vector-calculating section 5 evaluates what the degree of the damping effect caused by the distance from the individual microelectrode wires 4 to the nerve cell 3 for the individual signals (outputs of the channels) outputted from the individual amplifiers 2 is, without the evaluation being affected by a decrease in the signal-to-noise ratio, and it outputs a vector having the evaluated value as an element. For example, the covariances between the action potential waveforms observed from the channels and the template waveforms of nerve action potential spikes as shown in FIG. 3 are calculated, and the vectors, wherein the covariance values of the channels serve as elements, are outputted as space-damping vectors. Herein, as the template waveforms, it is preferable to use action potential waveforms that have been measured with the microelectrodes being satisfactory close to the cell, with the signal-to-noise ratio being high.

The above single-nerve action potential separating and extracting section 6 classifies the nerve action spikes based on the space-damping vectors obtained by the space-damping-vector-calculating section 5. For example, for the action potentials, the space-damping vectors are plotted in a pseudospace, and assuming that the nerve action spikes near the values of the space-damping vectors are generated from the same nerve cell, the nerve action spikes are classified by the corresponded relationship between the place where the distribution is concentrated and the cell.

Figure 2:
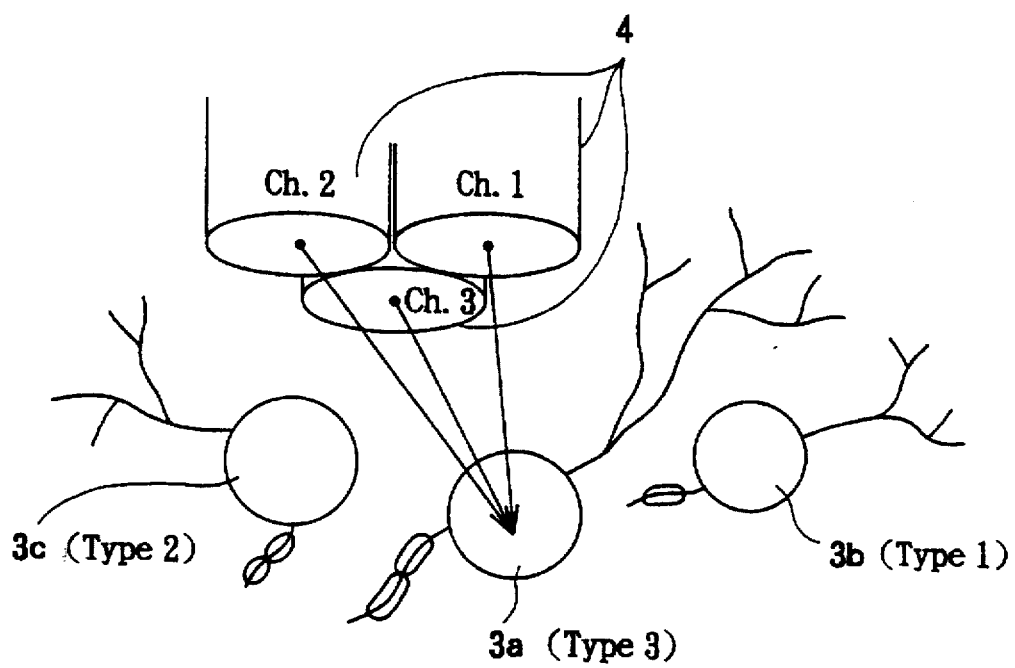
FIG. 2 is a diagram illustrating the damping effect due to the distance between the microelectrode and nerve cells.

Now, an example of the processing operation of the thus-constituted apparatus is described. It is assumed that each channel microelectrode 1 is made up of three microelectrode wires 4 (named ch1), 4 (named ch2), and 4 (named ch3), and the microelectrode 1 is inserted into a prescribed place in a brain or a nerve fascicle. At that time it is assumed that three cells $3a$, $3b$, and $3c$ are present near the microelectrode 1. Now, in FIG. 2, it is assumed that nerve excitation occurs, for example, in the cell $3a$. Since the nerve cell $3a$ is located closest to the electrode wire 4 (ch1) of the first channel and farthest from the electrode wire 4 (ch2) of the second channel, due to the damping effect in the space, a large action potential waveform is observed in the first channel (ch1), and a small active potential waveform is observed in the second channel (ch2). These action potential waveforms; that is, the multi-channel simultaneously measured data, are amplified by the amplifiers 2 at a certain amplification rate and are inputted into the space-damping-vector-calculating section 5. In the space-damping-vector-calculating section, the damping effect due to the distance between the electrode wires 4 and the cell 3 is calculated as an evaluation parameter, which is hardly affected by a decrease in the signal-to-noise ratio; that is, herein the said calculation is considered to be the covariance with the template waveform shown in FIG. 3. The covariance value indicates the amount of the template waveform component contained in the action potential waveform observed in the channels of wires 4 (ch1), 4 (ch2), and 4 (ch3); and in the above example, it is calculated as a large value from the action potential waveform in the first channel (ch1), and as a small value from the action potential waveform in the second channel (ch2). Herein, by using a typical action potential waveform as the template waveform, the influence that random noise or drift having waveform components different from the template waveform has on the evaluation value can be reduced. The thus-obtained covariance values of the individual channels are used as elements of vectors to obtain space-damping vectors. For example, in the example shown in FIG. 2, when the covariance values of the first, second, and third channels (ch1), (ch2), and (ch3) are found as cov (1), cov (2), and cov (3), respectively, the space-damping vector becomes [cov (1), cov (2), cov (3)]. Since these space-damping vectors are due to the positional relationship between the cells and the microelectrodes 1, a different cell produces a different vector value. That is, in FIG. 2, when nerve excitement occurs in a cell different from the cell 3a—for example, in a cell 3b—the space-damping vector is different from that obtained when nerve excitement occurs in the cell 3a. By using this, in the single-nerve action potential separating and extracting section 6, clustering is effected, and nerve action spikes can be classified for respective cells 3a, 3b, and 3c individually.

Figure 4:
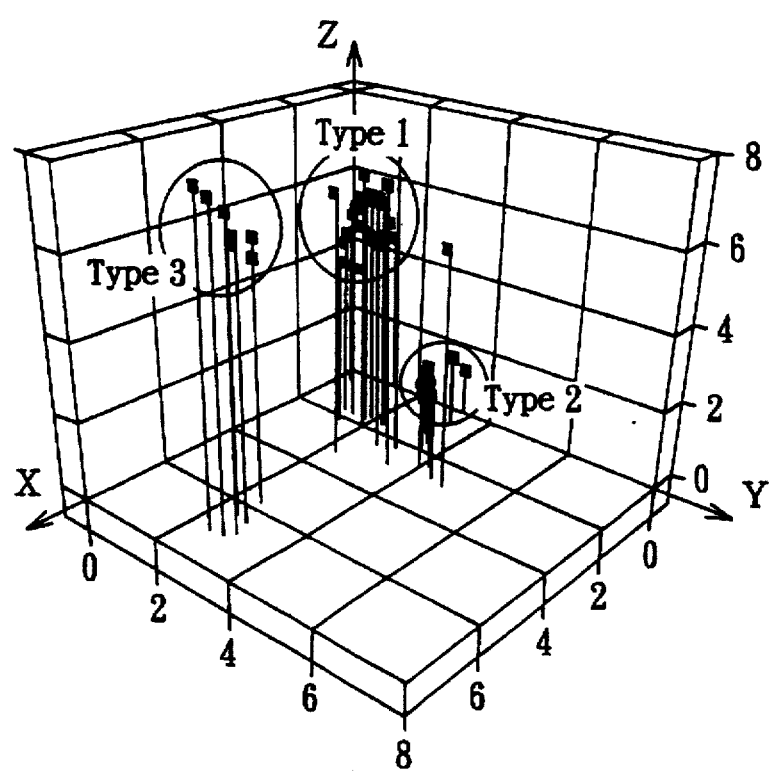
FIG. 4 is a diagram showing an example plot of the space-damping vectors.

FIG. 4 is obtained by plotting space-damping vectors with covariance values of the waveform of the first channel (ch1) and the template waveform shown in FIG. 3, using the actually measured results assigned to be values on the x-axis, and using covariance values from the second channel (ch2) and the third channel (ch3) assigned to be values on the y-axis and z-axis, respectively. From FIG. 4, it is confirmed that the concentrated sites of space-damping vectors corresponding to the cells 3a (type 3), 3b (type 1), and 3c (type 2) are formed.

Figure 5:
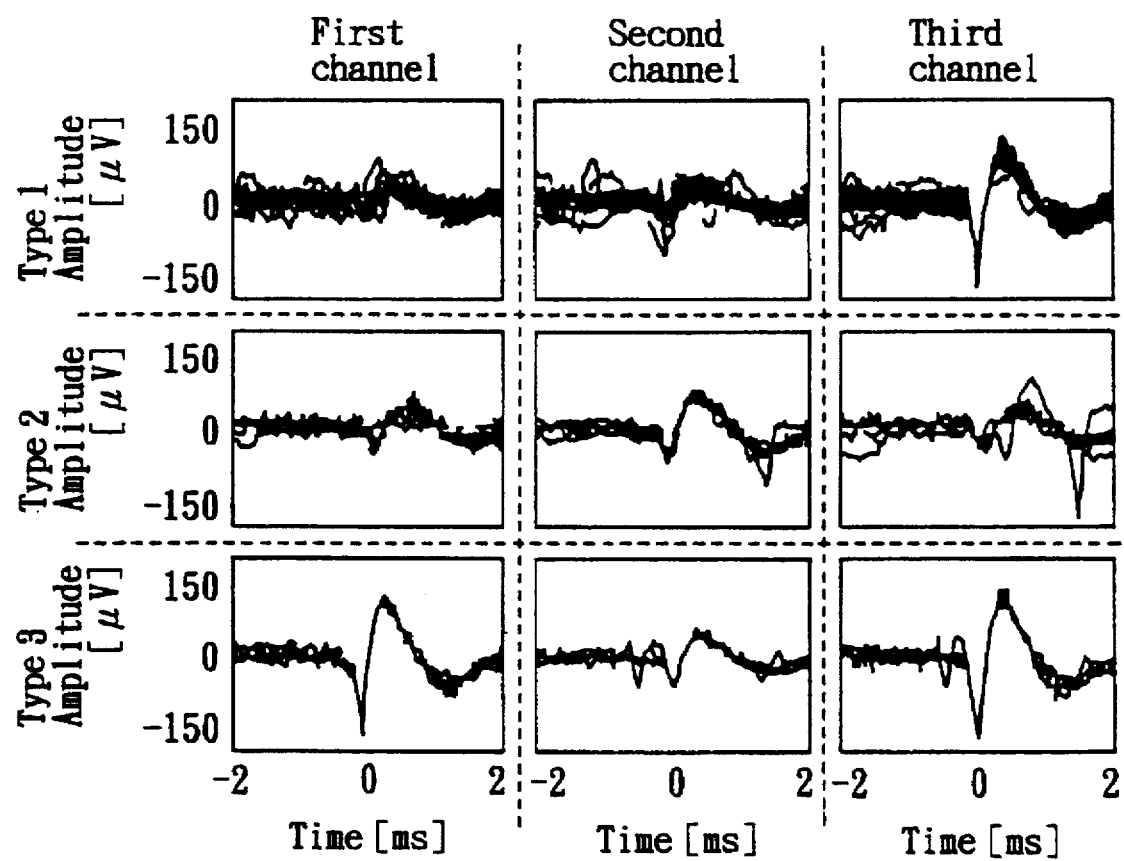
FIG. 5 is a diagram showing the result of the classification of action potential waveforms according to the present invention.

FIG. 5 is a diagram showing the classified result of nerve action spikes by clustering the result of FIG. 4 in the single-nerve action potential separating and extracting section 6. That is, FIG. 5 shows overlapped action potential waveforms of respective types observed from individual channels of wires 4 (ch1), 4 (ch2), and 4 (ch3) after clustering of types 1, 2, and 3, based on the space-damping vectors, similar to the results shown in FIG. 4. From this result, it can be understood that action potential waveforms generated from plural cells are classified for every cell. In particular, since the action potentials of the type 1 and type 3 in the third channel have almost the same waveform, they cannot be classified only by this channel information, but it is confirmed that they are classified easily by clustering by damping vectors and multi-channel measurement.

In the above mode of operation, although this is an example in which three cells are present near the microelectrode 1, if there are more cells near the microelectrode 1, nerve action spikes from multiple cells can be classified for the individual cells in a similar manner.

In such a single-nerve-action-potential measuring apparatus, multiple microelectrodes are placed in the space where measurement is to be made, and the nerve action spikes are separated based on the difference in the damping effect due to the difference of the distances between the electrodes and the nerve cells. Thereby, action spikes produced from multiple nerve cells present in the space where the measurement is to be made can be separated even under conditions of a low signal-to-noise ratio or at a brain site where cells are densely present.

As described above, according to the present invention, it is possible to easily classify nerve action spikes for every cell from multiple cells present near a multi-channel microelectrode for measuring the compound nerve action potential. The present invention is effective for a neuroelectricity physiology experiment when the signal-to-noise ratio is low or nerve cells are densely present.

Having described our invention as related to the present embodiments, it is our intention that the invention not be limited by any of the details of the description, unless otherwise specified, but rather be construed broadly within its spirit and scope as set out in the accompanying claims.

What we claim is:

1. A single-nerve-action-potential-measuring apparatus, comprising (A) a multi-channel microelectrode, for measuring the compound nerve activity, composed of multiple bunched microelectrodes to be inserted into a brain or nerve fascicle; (B) a space-damping-vector-calculating means, for evaluating the damping effect corresponding to the distance between the said multiple microelectrodes and nerve cells, based on the multi-channel simultaneously measured data led from the said multi-channel microelectrode, with no effect from a decrease in the signal-to-noise ratio; and (C) a single nerve action potential separating and extracting means, for separating and extracting the nerve action potential generated from a particular neuron from other neurons, based on the space-damping vector calculated in the space-damping-vector-calculating means.

2. The single-nerve-action-potential measuring apparatus as claimed in claim 1, comprising amplifiers for amplifying respective nerve action potentials led from the multi-channel microelectrode (A).

3. The single-nerve-action-potential measuring apparatus as claimed in claim 1, wherein the multi-channel microelectrode (A) comprises multiple microelectrode wires that are bunched.

4. The single-nerve-action-potential-measuring apparatus as claimed in claim 1, wherein the space-damping-vector-calculating means (B) further comprises means for calculating the covariances between action potential waveforms observed from the channels and template waveforms of nerve action potential spikes, to output vectors, in which the covariance values of the channels serve as elements, as space-damping vectors.

5. The single-nerve-action-potential-measuring apparatus as claimed in claim 1, wherein the single-nerve action potential separating and extracting means (C) (i) utilizes a plot in pseudo-space showing the space damping vectors for the action potentials, and assuming that the nerve action spikes with the similar values of the space-damping vectors are generated from the same nerve cell, and (ii) utilizes a distribution of the vectors and their relationship to the cell to classify nerve action spikes.

* * * * *